United States Patent [19]
Adkins et al.

[11] Patent Number: 5,928,272
[45] Date of Patent: Jul. 27, 1999

[54] AUTOMATIC ACTIVATION OF A NEUROSTIMULATOR DEVICE USING A DETECTION ALGORITHM BASED ON CARDIAC ACTIVITY

[75] Inventors: Robert A. Adkins, Angleton, Tex.; Cormac A. O'Donovan, Clemmons, N.C.; Reese S. Terry, Jr., Houston, Tex.

[73] Assignee: Cyberonics, Inc., Houston, Tex.

[21] Appl. No.: 09/071,856

[22] Filed: May 2, 1998

[51] Int. Cl.$^6$ .................................................. A61N 1/36
[52] U.S. Cl. ................................................................ 607/45
[58] Field of Search ................................................. 607/45

[56] References Cited

U.S. PATENT DOCUMENTS

| | | | |
|---|---|---|---|
| 4,702,254 | 10/1987 | Zabaza | 607/45 |
| 5,269,302 | 12/1993 | Swartz et al. | 607/45 |

*Primary Examiner*—William E. Kamm
*Attorney, Agent, or Firm*—Blank Rome Comisky & McCauley LLP

[57] ABSTRACT

A device and method of controlling seizures in an epileptic patient, in which the device is implanted in the patient for selective activation to generate an electrical waveform constituting a pre-programmed therapy regimen for application to the patient's vagus nerve to modulate the electrical activity thereof in a manner to inhibit, abort, or reduce the severity and duration of the seizure. The device is activated to generate the waveform upon detecting a time rate of change in the patient's heart rate relative to a predetermined threshold time rate of change which is sufficiently abrupt and of sufficient magnitude to be inconsistent with normal physical activity, as being indicative of an imminent epileptic seizure. Sustained cardiac activity at the highest heart rate detected in the change in heart rate is used as a confirmation of imminent seizure. The electrical waveform is generated a burst of pulses, with a minimum time interval between consecutive pulse bursts selected to avoid overstimulation of the nerve. Cardiac activity of the patient is detected using electrodes which include the conductive housing for the device and a stimulating electrode to be mounted on the nerve for large signal detection, or which are integral with the device housing itself so that no electrical leads are required to be implanted for such detection and the electrodes are arranged to detect the cardiac activity with a sensitivity that is substantially independent of orientation of the device as implanted in the patient.

27 Claims, 3 Drawing Sheets

AUTOMATIC ACTIVATION OF A NEUROSTIMULATOR DEVICE USING A DETECTION ALGORITHM BASED ON CARDIAC ACTIVITY

BACKGROUND OF THE INVENTION

The present invention relates generally to implantable battery-operated medical devices employed as neurostimulators for treating or controlling medical, psychiatric or neurological disorders by application of modulating electrical signals to a selected nerve or nerves of the patient, and more particularly, to improved methods and devices for activating a neurostimulator to treat an epileptic attack in response to the sensing of a natural activity of the body indicative of onset of such an attack.

Extra-physiologic electrical stimulation of the vagus nerve for treatment of epilepsy and various forms of involuntary movement disorders is disclosed in U.S. Pat. No. 4,702,254 to J. Zabara (referred to herein as "the '254 patent"), exclusively licensed to the assignee of the present application. A device constituting an implantable NeuroCybemetic Prosthesis (NCP™, a trademark of Cyberonics, Inc. of Houston, Tex.) generator activates or controls certain nerves of the patient—for example, by use of neurocybernetic spectral discrimination in which the external current of the NCP generator is tuned to the electrochemical properties of a specific group of inhibitory nerves that affect the reticular system of the brain. These nerves may be embedded within a bundle of other nerves, and are selectively activated directly or indirectly by such tuning of the NCP generator to augment states of brain neural discharge, by which to control convulsions or seizures. According to the '254 patent, the spectral discrimination analysis dictates that certain electrical parameters of the NCP generator are to be selected based on the electrochemical properties of the nerves desired to be activated.

Figure 1:
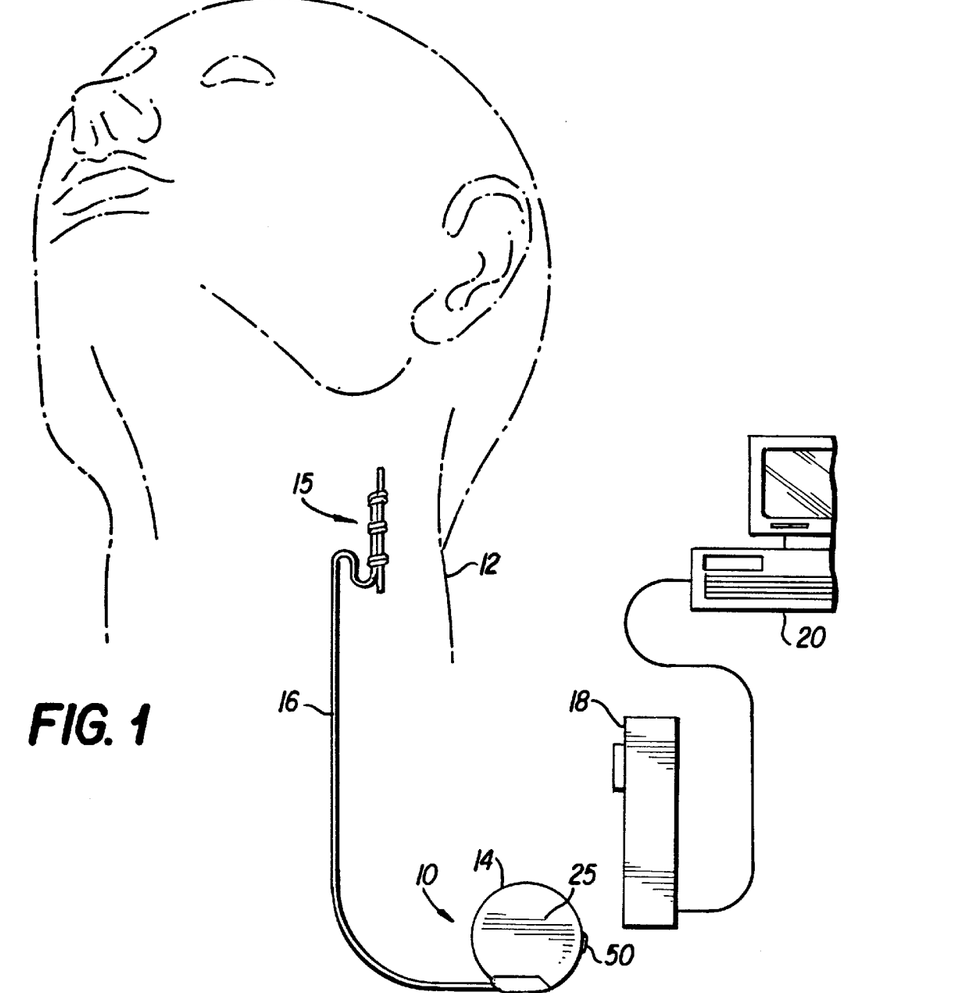
FIG. 1 is a simplified illustration of a neurostimulator device for stimulus generation with associated lead-electrode system implanted in a patient's body, together with related external program console as described in the background section above.

An improved implantable neurostimulator device is disclosed in U.S. Pat. No. 5,154,172 to R. S. Terry, Jr. et al. (referred to herein as "the '172 patent"), assigned to the assignee of the present application. The disclosure of the '172 patent is incorporated in its entirety by reference herein. In FIG. 1 of the accompanying drawings, a stimulus generator 25 and associated lead/electrode system 16/15 of a neurostimulator device 10 of the type generally disclosed in the '172 patent (but with certain improvements in sensing electrodes described in the detailed description of the invention below) are shown implanted in a patient.

Referring to the specifics of FIG. 1, the stimulus generator 25 portion of device 10, which is generally of thin circular, oval, or rectangular shape and suitably sized for implantation, is typically implanted within a surgically-formed pocket just below the skin in the left pectoral region of a patient 12. The back side of stimulus generator 25 (or the front side, depending on the implanting physician's preference as to the direction in which an electrically conductive insulatively sheathed lead 16 of the neurostimulator device 10 will extend for implantation of electrode array 15 of the lead on the vagus nerve or other selected cranial nerve of the patient) resides against the pectoral muscle in this example. The generator housing 14 (typically referred to in the art as a "can" or "case") is composed of biocompatible material (i.e., biologically compatible with the fluids and tissue of the patient's body), typically a metal such as titanium or medical grade stainless steel, and is hermetically sealed to prevent fluid penetration into the electronic components and battery(ies) (sometimes referred to herein as the "electronics package") contained therein.

A male connector at the proximal end of lead or lead assembly 16 is inserted into a female connector in a header 51 on case 14, to electrically connect the nerve stimulating electrode array 15 at the distal end of lead 16 to the proper node(s) of the electrical circuitry of the electronics package in the stimulus generator. The electrode array is preferably a bipolar stimulating electrode assembly, for example, of the type described in U.S. Pat. No. 4,573,481 to Bullara. The electrical output pulse waveform of stimulus generator 25 is applied through the lead-electrode system to a selected cranial nerve or nerve bundle of the patient on which the electrode array has been implanted, such as in the cervical location of the vagus nerve shown in FIG. 1.

The implanted neurostimulator device communicates by telemetry with a programmer and/or monitor (sometimes referred to herein as the "program console") external to the patient's body, by asynchronous serial communication, to selectively control and detect operating states of the device. Conventional external components employed for such purposes may include, for example, a programming wand 18 which transmits parameter changes to device 10 and receives device parameter and signal information to be monitored, in conjunction with computer 20 of the program console. Conventional software installed in the computer facilitates physician-controlled adjustment of selected parameters and of communication with the implanted device.

Figure 2:
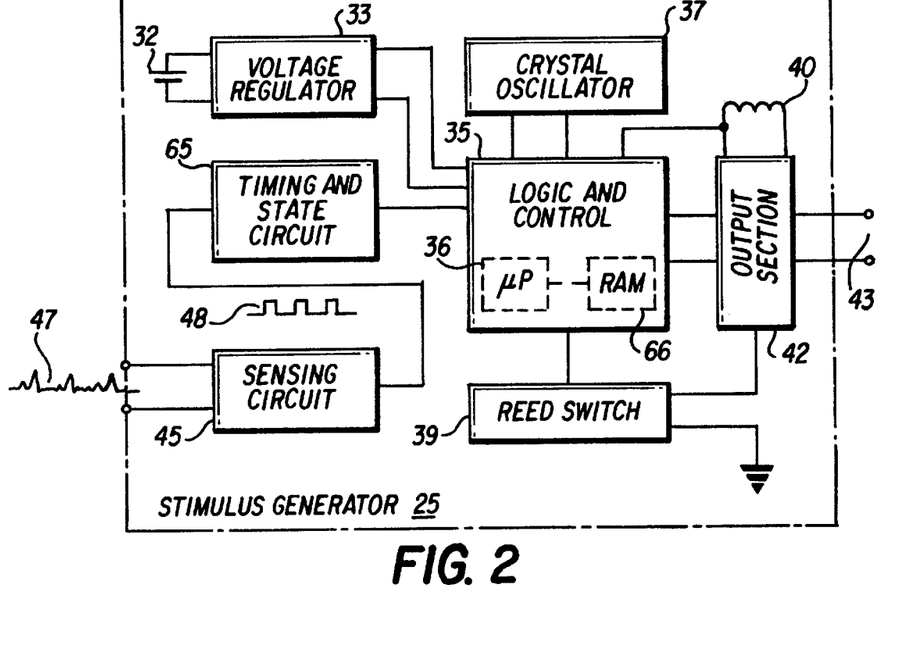
FIG. 2 is a simplified block diagram of an implantable stimulus generator of the type used in the device of FIG. 1, described in the background section above, to the extent of a prior art portion, and utilizing a sensing circuit according to the present invention.

A simplified block diagram of the stimulus generator 25 of implantable device 10 is illustrated in FIG. 2. The stimulus generator includes battery(ies) 32, such as a lithium carbon monofluoride cell, electrically connected to the input of a voltage regulator 33, which powers the device. The regulated output voltage is supplied to a logic and control section 35 and other electronic sections, including a microprocessor 36 that implements and controls the programmable functions of the device. Programmable functions may include the magnitude of current or voltage, the frequency, the pulse width, and the on-time and off-time of output pulses generated by the stimulus generator for application to the lead assembly and thence to the distal electrode array and the nerve on which it is implanted. The programmability of the device enables the attending physician to selectively tailor its output pulse waveform to modulate the electrical activity of the vagus nerve to provide a prescribed therapy regimen for the disorder being treated—epilepsy, in this case. Timing of the logic and control and other functions of the stimulus generator is controlled by a precise output frequency signal of a crystal oscillator 37. A magnetically-actuatable reed switch 39 enables the patient to manually activate the generator for initiating the delivery of its output pulses to the nerve by means of an external magnet (not shown).

Built-in antenna 40 is provided for use in bidirectional telemetry communication between the implanted stimulus generator and the external electronics of the program console, for supplying the programming signals necessary to set or change the output pulse parameters, and to detect device operation, via wand 18 (FIG. 1). Once the generator is programmed, it operates continuously at the programmed settings until they are re-programmed (by the attending physician) by means of the external program console.

Logic/control section 35 controls output circuit 42 for producing the output pulse waveform according to the prescribed therapy. When the stimulus generator is activated, which may be continuously or periodically to provide prophylactic/preventive treatment of the disorder, or which may be controlled by the patient's manual activation or by automatic activation upon sensing physiologic changes indicative of onset of the disorder, the programmed output waveform is delivered via the electrical connector in the header of the generator case to lead assembly 16 and stimulating electrode array 15 (FIG. 1). This electrical stimulation produces a predetermined modulation of the electrical activity of the nerve on which the electrodes are implanted to treat, control, and alleviate the disorder. Where the patient is being treated for epileptic seizures, for example, the electrical activity of a cranial nerve such as the vagus nerve is modulated by initiation of the stimulus waveform in response to a set of detection criteria having been met, for the purpose of inhibiting or interrupting a seizure, or of lessening the frequency or severity of seizures.

Certain techniques of manual and automatic activation of implantable medical devices are disclosed in U.S. Pat. No. 5,304,206 to R. G. Baker, Jr. et al. (referred to herein as "the '206 patent"), which is assigned to the same assignee as the present application. The '206 patent discusses problems that may be encountered when a patient seeks to manually activate the device upon sensing onset of the disorder, such as quickly locating the magnet; as well as the surgical procedural problems experienced where special sensors such as EEG electrodes are sought to be implanted for automatic activation. According to the invention disclosed in the '206 patent, means for manually activating or deactivating the stimulus generator include a sensor such as an accelerometer or a piezoelectric element mounted to the inner surface of the generator case and adapted to detect light taps by the patient on the implant site. In this way, the patient is given limited but convenient control over the device operation, to an extent which will be determined by the attending physician. The '206 patent also discloses an automatic activation technique for the implanted device, in which random jerky movements of the patient that occur with some types of seizures, and which are not consistent with normal activity, are detected by a vibration sensor, accelerometer, or other means having programmable sensitivity. The sensor may thus be fine-tuned to the seizure characteristics of a particular patient without likelihood of being triggered by normal activity of the patient.

The present invention is directed toward further improvements in automatic activation of an implanted neurostimulator device, particularly for treating epilepsy. A principal objective of the invention is to provide apparatus and methods for activation of an implanted stimulus generator for treating epileptic seizures by sensing changes in certain physiological parameters which can be a reliable precursor of an oncoming attack.

SUMMARY OF THE INVENTION

The present invention is based upon the premise, borne out by empirical evidence, that the heart rate of an epileptic subject undergoes a sudden, rapid rate of change to an elevated rate immediately before or at the onset of a seizure. More broadly, according to the invention, the patient's cardiac activity is monitored, preferably by an implanted device, for characteristics of a sudden time rate of change of heart rate not physiologically consistent or compatible with physical exercise—most generally, a positive increase in time rate of change (i.e., slope, or first derivative) of heart rate, although a decrease (negative slope) in rate of change having those characteristics is also possible—and, to a lesser extent, a change in heart rate itself which is substantial and sustained. If such a time rate of change is detected, together with a substantial, sustained change (typically, an increase) in heart rate, the device is arranged and adapted to respond with neurostimulation, and more specifically, to initiate stimulation of the patient's vagus nerve to modulate the electrical activity thereof according to a programmed impulse waveform for treating the expected impending seizure.

Although the precise mechanism responsible for the sudden time rate of change of the patient's heart rate as a precursor of a seizure is not fully understood at this time, we hypothesize that it is likely to be attributable to an instability of autonomic tone caused by electrical activity associated with a seizure. Characterizing this as an instability of autonomic tone is, in part, an uncertainty regarding the relative contributions of sympathetic and parasympathetic influences. It is also possible that an instability of autonomic tone and accompanying rapid rate of change of heart rate precede (i.e., are a precursor of) a sudden change in the patient's electroencephalogram (EEG) or other physical manifestation of seizure activity, such as uncontrollable violent movements. If so, initiating the administering of the prescribed neurostimulation therapy would be accomplished that much earlier, with a greater likelihood that the seizure will be, if not inhibited, aborted relatively soon after its onset, or at least reduced in severity or duration.

In a presently preferred embodiment of the invention, the device has or is electrically connected to one or more sensing electrodes for measuring the electrical waveform associated with cardiac activity of the heart. The metal case of the stimulus generator can be used as one sensing electrode of a bipolar configuration. In one implementation, the sensing is between the metal case and an active electrode of the array mounted on the vagus nerve, which serves to detect a large cardiac signal. The side of the case facing the ribs, when the generator is implanted, is coated with electrically insulating material to inhibit muscle stimulation from electrical activity of the generator. This also aids the sensing process. In another implementation, two sensing electrodes are utilized to detect the EKG (ECG) signal, to ensure that the detection is accomplished independent of the alignment of the implanted device in the body of the patient, and independent of the direction of the electric field gradient attributable to the cardiac activity. Preferably, these electrodes are located at predetermined spaced-apart points along the exterior of the device case, and not on a separate lead or leads external to the case. As a result, the only lead required to be implanted in the patient is the lead associated with the electrode array to be implanted on the vagus (or other cranial) nerve for stimulation thereof A signal obtained from the intrinsic cardiac activity (the "sense signal") is processed by the implanted device to develop and store a running average of heart rate, both short term and longer term, each with a programmable time constant. Because heart rate is typically lower when the patient is in a sleep state, these running averages may be used as a first order detector of patient sleep, to initiate delivery of nerve stimulation as a prophylactic measure.

The short term running average is continuously compared within the device electronics to the long term running average, which aids in detecting an occurrence of sudden significant rate of change of heart rate (typically, as noted above, a positive slope) exceeding a programmed threshold level (e.g., a predetermined grade) that is taken to indicate onset of epileptic seizure. The programmed threshold may, for example, be set at a slope or grade representative of, say, an increase in absolute heart rate from 80 beats per minute (bpm) to 100 bpm in a period of a few (e.g., ten) seconds. Such a sudden rate of change is much more pronounced than a change prompted by physical exercise, and although it could represent pathologic tachycardia or fibrillation attributable to cardiac disease or disorder, for an epilepsy patient with no history of such disease or disorder it is deemed to be indicative of a need for immediate therapy to prevent or alleviate an imminent seizure. Upon that occurrence, a microprocessor initiates activation of a stimulus generator in the device to apply the pre-programmed electrical waveform stimulus therapy to the electrode array implanted on the patient's vagus nerve, to appropriately modulate the nerve's electrical activity to inhibit, abort, or alleviate the seizure.

Even if not applied early enough to inhibit an impending seizure or to abort a beginning attack clinical studies conducted on behalf of the assignee of the present application have demonstrated that a treatment regimen including application of appropriate vagal stimulation at or soon after onset of a seizure can be effective to reduce the severity and/or duration of the seizure in a significant percentage of the epilepsy patient population. Prophylactic application of such therapy has also been shown to reduce the frequency of the seizures, and animal studies of vagal stimulation show some promise that such a regimen may be effective to provide longer-lasting moderation of seizures.

While it is presumed that a positive slope in a sudden time rate of change of the patient's heart rate is the more likely precursor of an imminent seizure, it is also possible that a negative slope (i.e., indicative of a sudden drop in absolute heart rate) may have legitimacy in that regard. For patients in the latter class, an alternative embodiment of the implanted device is programmed to trigger neurostimulation upon detection of a sudden significant negative slope in the time rate of change of heart rate exceeding (i.e., in a negative direction) the programmed threshold level, or grade, deemed to indicate onset of epileptic seizure. In response, the stimulus generator is activated to apply the pre-programmed electrical waveform stimulus to the nerve electrode array, with the above-described effect. On the premise that treatment is not harmful even if the detected cardiac activity is a false indication of an oncoming seizure, the device may be programmed to stimulate and appropriately modulate electrical activity of the vagus nerve whenever the patient's heart rate exceeds or falls below the applicable programmed positive or negative slope threshold. The device may additionally be programmed to apply a periodic prophylactic stimulation of the nerve or nerve bundle to modulate its electrical activity in an appropriate manner for inhibiting seizures while the patient is sleeping, the sleep state being recognizable as a sustained period during which the sense signal is indicative of a heart rate lower by a predetermined margin than the average long term heart rate.

Accordingly, it is a more specific aim of the present invention to provide methods and apparatus for automatically and selectively modulating the electrical activity of a cranial nerve, preferably the vagus nerve, of the epileptic patient in a predetermined manner in response to detection of a sudden time rate of change of the patient's heart rate, to inhibit, abort or alleviate a seizure. Detection of such rate of change of heart rate, coupled with detection of a substantial and sustained increase in absolute heart rate, offers relative ease of detection, reliability as an indicator, and simplicity of the sensor and implant procedure.

In an alternative embodiment of the invention, the sensed cardiac activity signal is subjected to spectral analysis, with particular attention devoted to the higher frequency band. If the high frequency peak of the cardiac activity exhibits an increase of predetermined magnitude and duration, this is deemed to be indicative of an oncoming seizure, and the stimulus generator is activated to apply its electrical output stimulus to the lead/electrode array and, thence, to the vagus nerve so as to suppress the seizure or to minimize its effect. On the other hand, if the high frequency peak displays a change, but in the form of a decrease in magnitude, the change is assumed to be induced by a commencement of physical activity or exercise by the patient. In the latter case, no vagal stimulation is initiated.

It is therefore a further objective of the invention to initiate vagal stimulation of an epileptic patient according to an algorithm based upon spectral analysis of the cardiac activity signal of the patient.

BRIEF DESCRIPTION OF THE DRAWINGS

The above and other aims, objectives, aspects, features and attendant advantages of the invention will be further understood from the following detailed description of the best mode presently contemplated for practicing the invention, by reference to a presently preferred embodiment and method, taken in conjunction with the accompanying drawings, in which.

DESCRIPTION OF THE PRESENTLY PREFERRED EMBODIMENT AND METHOD

Figure 4:
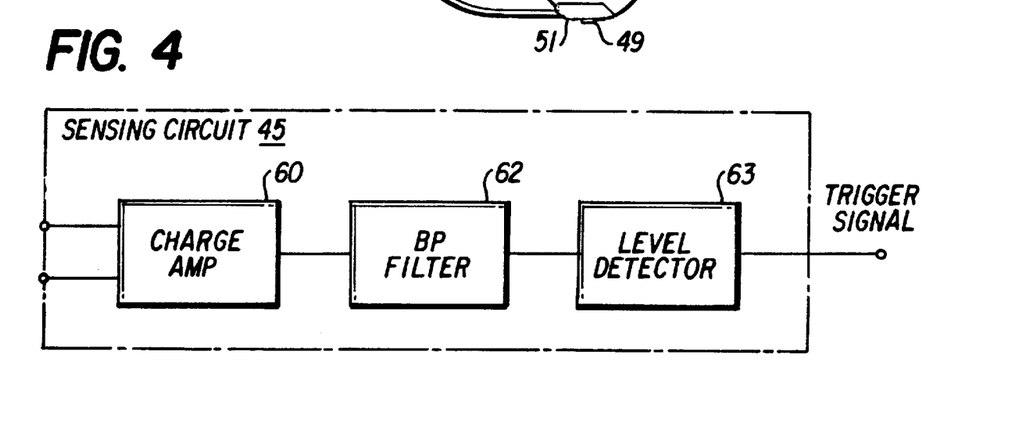
FIG. 4 is a simplified block diagram of a sensing circuit used in the stimulus generator of FIGS. 2 and 3.

Referring again to FIG. 2, distinct from the prior art, the stimulus generator 25 of a neurostimulator device 10 of the preferred embodiment of the invention includes a sensing circuit 45 for measuring the electrical signals 47 indicative of the patient's cardiac activity (e.g., as the EKG, or ECG). Details of the sensing circuit will be discussed in greater detail in the description of FIG. 4, below. For the present, however, it is sufficient to note that the circuit responds to an input exceeding a preset threshold slope (and also, if desired, detection of a sustained higher absolute heart rate) by producing a logic level output. The logic level output signal 48 is applied to a timing and state circuit 65 which is also arranged to receive a signal representing heart rate sequence similar to that applied to the sensing circuit, and to supply an output to logic and control section 35 from which the output circuit 42 is controlled. Operation of circuit 65 will be described in greater detail presently, with reference to FIG. 5.

Figure 3:
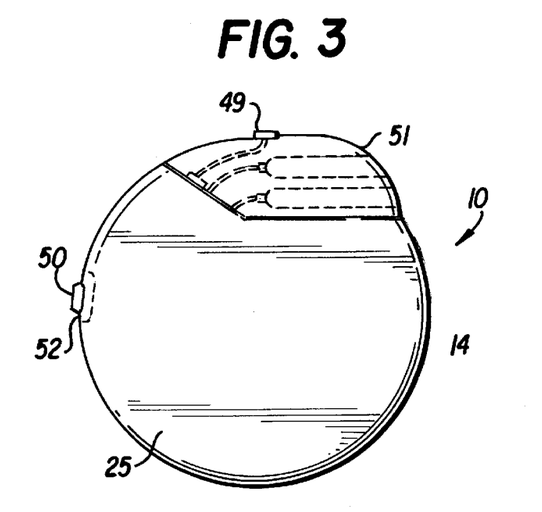
FIG. 3 is a side view of the front of the stimulus generator case showing the location of one set of sensing electrodes on the exterior of the generator according to the present invention.
Figure 3A:
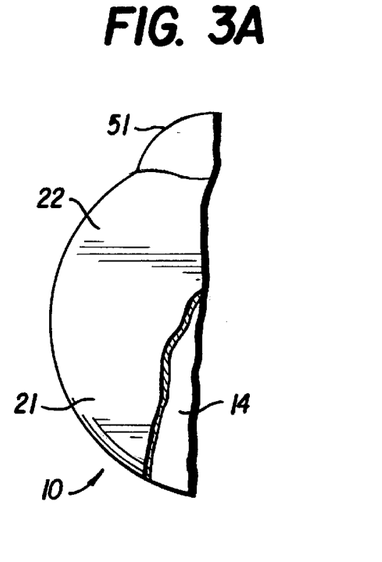
FIG. 3A is a fragmentary view of the back side of the case.

A view of the front side of an implantable stimulus generator 25 of a neurostimulator device 10 implemented to treat epileptic seizures according to the invention is illustrated in FIG. 3. The generator 25 is equipped with one or more sensing electrodes for measuring the electrical impulses constituting the cardiac activity of the heart. In a presently preferred embodiment, the metal case (generator housing) 14 is used as one sensing electrode in either of two sensing implementations. In a preferred one of two alternatives, sensing is performed between metal case 14 and one of the two active (stimulating) electrodes of array 15 (FIG. 1) that are connected to the vagus nerve. These electrodes, when used for sensing, are positioned to detect a relatively large cardiac signal. In this alternative, the back side 21 of case 14 of generator 25, shown in FIG. 3A, is preferably coated with a layer of biocompatible, electrically insulating material 22 of any conventional type for such purpose and use, to minimize muscle stimulation. To that end, the generator would be implanted with the insulated back side 21 facing "down", i.e., inwardly, toward the patient's ribs.

In the other sensing alternative, a pair of additional sensing electrodes 49, 50 are exposed at the exterior surface of the case, one located in the header 51 and the other on the main body of the case but insulated therefrom, preferably along the edge of the case, so that the electrodes are positioned for greater sensitivity to the electrical activity of the heart regardless of whether the generator is implanted with the front (logo) side "up" (facing outwardly of the patient's body), or down. Also, the exterior electrodes 49, 50 are preferably displaced by about 90 degrees (orthogonally) from each other about the periphery of the case along its edge, as shown in FIG. 3, to assure good sensitivity regardless of the orientation or alignment of the case relative to the field produced by the cardiac electrical activity. The purpose of these procedures is to enhance the detection of the cardiac signal by positioning the electrodes to be at points of its greatest magnitude.

Each of these electrodes is electrically isolated from the metal case 14. Isolation of electrode 50 is achieved by use of an electrical insulator 52 positioned between the electrode and the case, which is also implemented to provide a tight seal against intrusion of body fluids into the interior of the case. Electrode 49 is electrically insulated from the case by virtue of the electrically insulating character of the header 51 itself. The two external electrodes 49, 50 may be connected in parallel so that they act effectively as a single additional electrode (i.e., additional to the electrode provided by the metal case itself).

An important aspect of the invention is that the sensing and automatic activation capability is provided upon implantation of the stimulus generator alone, without need for implantation of a separate lead and electrodes in direct contact with or in proximity to the heart. The sensing electrodes, one of which is the stimulating electrode, or which are the two electrodes positioned externally on and electrically insulated from the case, are able to detect the electrical activity of the heart in the same way as a surface electrogram is obtained.

The sense signal is supplied to a microprocessor 36 within the stimulus generator housing, to receive and record signal information indicative of the patient's heart rate, and time rate of changes thereof, and to maintain an ongoing average of both short term and long term heart rate with a programmable time interval for each. For the short term average, the monitoring preferably ranges up to 32 beats, and for the long term average, up to 124 beats. It may desirable to assess a twenty-four hour average with calculation of a standard deviation for modification of the trigger slope.

Monitoring short term average and calculations based thereon tends to decrease occurrence of false positives, with some reduction in sensitivity of detection. In any event, failure to detect an imminent seizure will result in a missed opportunity to abort the seizure, which is more significant than neural stimulation in response to false positives because the latter is not likely to produce harmful side effects. Also, the capability to more quickly detect onset of seizures is significant because animal studies have shown that reducing the time interval of detection and stimulation increases the likelihood of aborting the seizure.

With an automatic detection algorithm based on sudden rate of change as in the system and method of the present invention, an overly high sensitivity might result in continuous therapy. Preferably, the time interval between consecutive applications of nerve stimuli should be programmed to assure that a suitable minimum off time is provided to prevent overstimulation.

Rate of change of heart rate over the short term running average is continuously compared to the same calculation for the long term running average. If it is determined that a sudden change in heart rate surpasses the programmed threshold slope, the programmed therapy waveform is applied to the nerve electrode. In the preferred embodiment of the invention, slope detection is readily performed by the microprocessor 36 in conjunction with the control circuit. This is preferred because the microprocessor is easily programmed, and such a technique and arrangement has the additional advantage of requiring fewer components and thus allowing implementation of the generator in a smaller package.

The use of additional noise elimination algorithms may be desirable. A sudden increase followed by a sudden decrease within a very short period of time may be attributable to movement artifacts. A requirement for a sudden and sustained increase or decrease in rate would serve to reject this type of noise. In any event, the algorithm should have characteristics of a capability to distinguish between increases that result from exercise or activity of the patient, as well as normally expected heart rate variability, and noise artifacts. For example, a 50 msec or greater change in interval between heart beats may be associated with breathing in normal healthy subjects.

External electrodes 49 and 50 (connected in parallel) and case 14, or one of the nerve electrodes and the case, are electrically connected to the input terminals of sensing circuit 45 (FIG. 2). As an alternative to use of the microprocessor for detection of the slope, which is preferred, the sensing circuit may be implemented to provide an analog detection circuit. Referring to the simplified block diagram of the sensing circuit in FIG. 4, the sense signal derived by the respective sense electrodes is applied to a charge amplifier (e.g., a capacitive ramp generator) 60 having a fixed time constant for periodically generating slopes of heart rate over time. The output of the latter circuit is filtered by a slope detection filter 62 to examine only slopes indicative of rate changes in a preselected range above those reflecting normal exercise or activity, even of a strenuous nature. Each such slope (ramp) is compared in a ramp comparator 63 to a programmed threshold slope and, if the threshold is exceeded, to trigger the deliver of the therapeutic stimulus to the nerve electrode. The sensitivity of sensing circuit 45 may be varied by appropriately programming the gain of amplifier 60 and/or by adjusting the threshold slope of detector 63, using the external programming console.

The selectively of sensing circuit 45 in distinguishing seizure-induced rate of change of the patient's heart rate from change attributable to normal physical activity may be enhanced by the provision of timing and state circuit 65 (FIG. 2). The latter circuit also receives the rate sequences indicative of cardiac activity from the sensors, as well as monitoring the output signal of sensing circuit 45. Circuit 65 also operates in conjunction with microprocessor 36 and associated random access memory (RAM) 66 within the logic and control section 35 of the stimulus generator.

Figure 5:
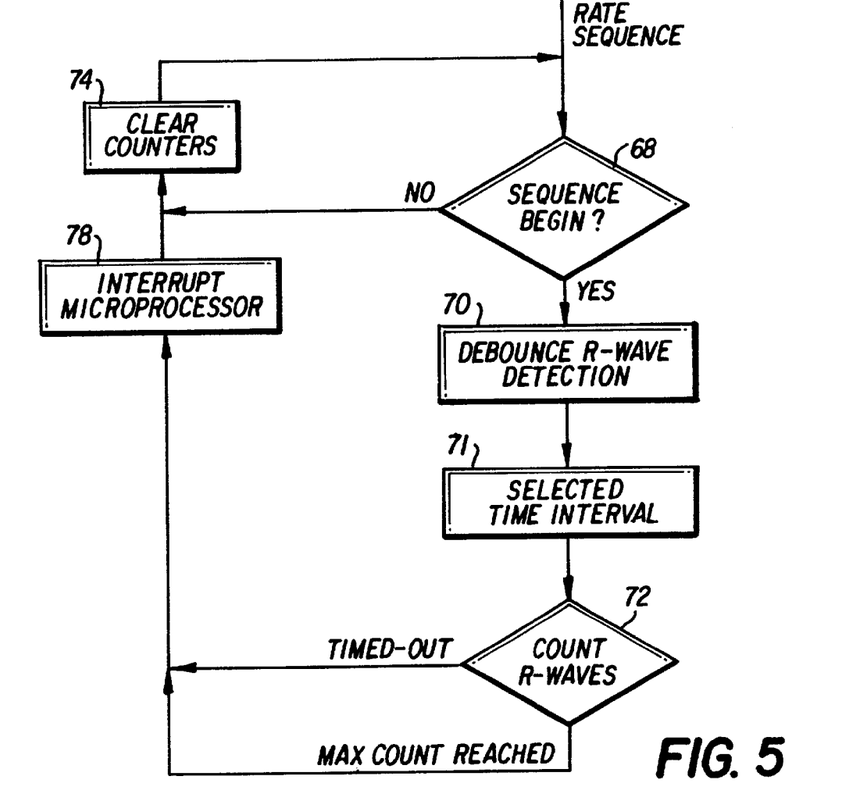
FIG. 5 is a flow diagram of the operation of a timing and state circuit used in the stimulus generator of FIG. 2 to assist the sensing circuit in distinguishing seizure-induced changes in cardiac activity, which may be detected in the patient's EKG, from the normal physiologic tachycardias attributable to patient exercise.

Operation of timing and state circuit 65 is illustrated by the flow chart of FIG. 5. Implementation of a circuit and/or software to perform the functions of the timing and state circuit according to this flow chart are readily achieved in various well known ways. The circuit 65 is essentially a multi-state machine which waits in the ready state 68 for each heart rate sequence to begin. In the ready state, a counter is initially cleared in advance of each input rate sequence to count R-waves in the patient's cardiac activity sense signal over a predetermined time interval. A timer having a predetermined maximum time interval (at which the timer "times out") is also held in a cleared state in preparation for measuring the time elapsed from the start of the latest time measurement interval in a sequence of such intervals.

Detection of the first R-wave in the predetermined time interval moves the state machine to a waiting state (70) in which the R-wave detection is "debounced" to enhance detection of each R-wave as a single event. On expiration of a preselected time interval of only a few milliseconds of the time counter (71), the state machine enters an increment state (72) in which the R-wave counter is incremented by one with detection of each individual R-wave. The increment state is exited upon the occurrence of either of two different conditions.

If either a predetermined maximum count of R-waves by the counter takes place before the timer times out (i.e., before the predetermined interval of the timer elapses), or if the timer times out, the cardiac activity sequence of interest is examined to assess whether the patient's heart rate is undergoing a time rate of change which is consistent or inconsistent with physical exercise (e.g., walking, or even merely getting up from a sitting or lying position), or the heart rate is relatively constant so that no rate of change is being experienced. Occurrence of either of the first two conditions will produce an exit and cause an interrupt of the microprocessor (state 73) in the logic and control section.

The R-wave count is divided by the time interval (either the time out interval or the interval up to the point that the maximum count is reached, as applicable), and the result is assessed to determine whether a rate of change of heart rate occurred in the latest rate sequence which meets the criteria for suddenness and is inconsistent with exercise, but rather, a precursor of imminent epileptic seizure. An exercise-induced rate of change of heart rate will occur over a considerably longer interval of time than a change of the same absolute magnitude which is induced by an impending seizure. At the same time that the calculation is performed for the old rate sequence, the counters (including timer) are cleared in preparation for analyzing a new window of cardiac activity, and the microprocessor resets the state machine to the ready state 68.

If the microprocessor and associated logic control circuitry determines that the threshold slope (rate change) is exceeded (either independently, as is preferred, or confirming the finding of the sense circuit), the programmed nerve stimulation waveform is triggered. As an additional check, the absolute heart rate is monitored by the timing and state circuit to assess whether, when the threshold slope is exceeded, the rate is sustained for a preset interval of time. If so, the stimulus is generated from the output section of the implanted device in the form of the selected waveform therapy to appropriately modulate the vagal activity, whereby to inhibit a seizure if it has not commenced, or, if it has commenced, to abort it or reduce its severity and/or duration.

Clinical evaluations of patient responses have indicated that stimulation pattern (pulse) sequences ranging from "on" time of 30 seconds followed by "off" time of five minutes, to "on" time of seven second followed by "off" time of 14 seconds, are well tolerated and within a range of suitability to achieve the desired effect. In a free running mode in which such a pattern sequence has been preselected for delivery as the desired therapy for a particular patient, there is little risk of overstimulation. Additionally, side effects of stimulation such as voice modulation and hoarseness can be minimized by known techniques, and are virtually eliminated where the vagal stimulation is triggered solely by the threshold detection (in contrast to prophylactic treatment).

A different automatic detection algorithm, or manual activation may be used in cases where the epileptic patient is also suffering from heart disease or disorder of a type which would render the cardiac activity algorithm inconclusive. Spectral analysis of heart rate variability may provide greater sensitivity for discrimination between exercise-induced and seizure-induced rate changes, but involves a more complex structure and analysis. It is postulated that a seizure-induced rate change increases the high frequency peak of the high frequency band of the spectrum, whereas an exercised-induced rate change causes a decrease in such peak of the high frequency band. Subjection of the detected cardiac activity to spectral analysis to differentiate between exercise-induced and seizure-induced changes in a patient's cardiac activity is illustrated in the block diagram of the alternative embodiment of FIG. 6.

Figure 6:
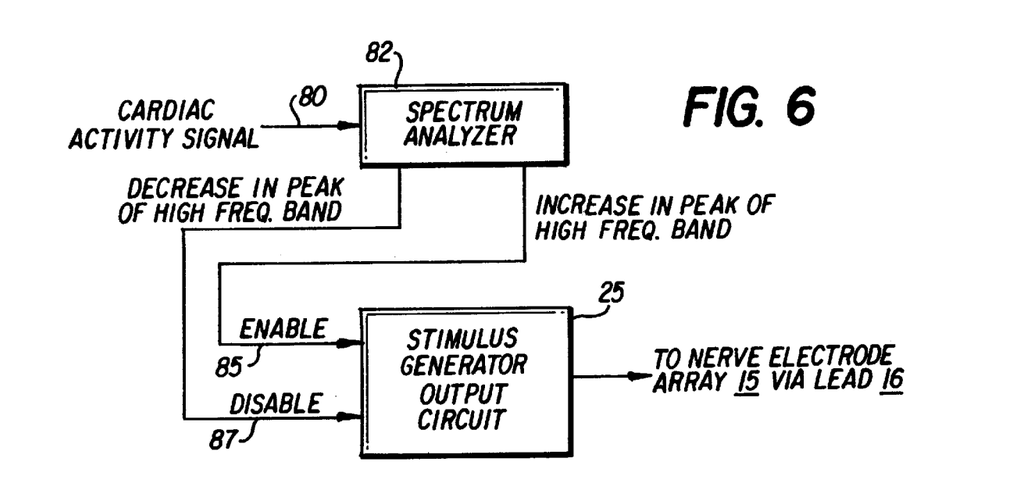
FIG. 6 is a simplified block diagram of an alternative embodiment in which the detected cardiac activity is subjected to spectral analysis to differentiate between exercise-induced and seizure-induced changes in a patient's cardiac activity.

In FIG. 6, the sensed cardiac activity signal 80 is applied to a spectrum analyzer 82. The output of the analyzer is used to trigger vagal stimulation by the implanted stimulus generator 25 according to whether the signal 80 exhibits an increase in the high frequency peak of the high frequency band. If it does, the output stimulus of the generator 25 is enabled by a trigger signal at 85 to deliver the designated pulsed output to the nerve electrode array 15 via lead assembly 16 and, thus, to modulate the electrical activity of the vagus nerve in a manner to inhibit or suppress the oncoming seizure before the seizure can fully manifest itself in the patient's brain. In contrast, if by virtue of the spectral analysis cardiac activity signal 80 is detected to undergo a time rate of change of heart rate which exhibits a decrease in the high frequency peak of the high frequency band, the change is deemed to be exercised induced, and the stimulus generator 25 is disabled from generating its output stimulus by a disabling input signal applied at 87.

Although a preferred embodiment and method have been described herein, it will be apparent to persons skilled in the art of the invention, from a consideration of the foregoing disclosure, that variations and modifications of the disclosed embodiment and method may be made without departing from the spirit and scope of the invention. Accordingly, it is intended that the invention shall be limited only to the extent required by the appended claims and the rules and principles of applicable law.

What is claimed is:

1. A medical device for treating an epileptic patient, comprising:

implantable electronic means housed in a case substantially impervious to body fluids and tissue and operative when activated for generating selected ones of electrical waveforms representing preprogrammed therapy regimens to control epileptic seizures;

implantable lead means adapted for electrical connection to the electronic means via an electrical connector mounted on the case thereof, for delivering selected ones of said therapy regimens to a preselected cranial nerve of the patient to electrically stimulate and thereby modulate electrical activity of the selected nerve in a manner which is predetermined to control seizures;

said electronic means including means for detecting time rate of change of the patient's heart rate from cardiac activity, and activation means responsive to detection of a sudden time rate of change of heart rate which is inconsistent with normal physical activity of the patient, as being indicative of an impending seizure, for automatically activating the electronic means to generate a selected one of the therapy regimens for application to said lead means, whereby to deliver a desired stimulus to the selected cranial nerve.

2. The medical device of claim 1, wherein:

said detection means includes means for assessing the time rate of change of detected cardiac activity relative to a preset threshold slope indicative of an impending seizure.

3. The medical device of claim 2, wherein:

said detection means comprises a microprocessor.

4. The medical device of claim 1, wherein:

said detection means includes means for analyzing the high frequency portion of the spectrum of detected cardiac activity for indication of an impending seizure.

5. The medical device of claim 1, wherein:

the detection means includes electrode means integral with and electrically insulated from said case, including first and second electrodes spaced apart on the case and electrically connected in parallel to detect cardiac activity independent of the orientation of the case as implanted in the patient.

6. The medical device of claim 5, wherein:

the case is electrically conductive for use as an additional electrode to detect cardiac activity of the patient.

7. The medical device of claim 5, wherein:

one of said first and second electrodes is located on the case at an electrically insulative header in which the electrical connector for the electronic means is mounted.

8. The medical device of claim 1, wherein:

the lead means has a proximal end and a distal end, the proximal end including an electrical connector for mating with the electrical connector on the case, and the distal end including a nerve electrode constructed and adapted to be implanted on the patient's vagus nerve for stimulation thereof as the selected cranial nerve.

9. The medical device of claim 8, wherein:

said electrode means includes the nerve stimulating electrode.

10. An electrical stimulus generator adapted for implantation in a patient suffering from epilepsy, to provide electrical stimuli for application to a selected cranial nerve as a therapy to alleviate a seizure, the stimulus generator comprising:

electronics effective when energized for generating said electrical stimuli;

an electrically conductive case housing said electronics; and electrode means electrically connected to said electronics for sensing cardiac activity of the patient, said electronics including means responsive to sudden time rate of change of the patient's heart rate in the sensed cardiac activity for distinguishing a change which is a precursor of an imminent epileptic seizure from a change attributable to normal physical exercise, to energize the electronics to generate said electrical stimuli upon the seizure-indicative change.

11. The stimulus generator of claim 10, wherein:

said distinguishing means comprises a microprocessor.

12. The stimulus generator of claim 10, wherein:

said distinguishing means comprises means for identifying a seizure-indicative change from its slope relative to a threshold slope representative of a reference time rate of change.

13. The stimulus generator of claim 10, wherein:

said distinguishing means comprises spectrum analyzer means for distinguishing a seizure-indicative change from an exercise-indicative change by the direction of a change in high frequency peak of the high frequency portion of the spectrum of cardiac activity.

14. The stimulus generator of claim 10, wherein:

said electrode means includes first and second electrodes mounted on and electrically insulated from said case; said first and second electrodes being electrically connected in parallel and adapted to cooperate with said case as an additional electrode with sufficient sensitivity to detect the patient's cardiac activity independently of the orientation of the implanted stimulus generator.

15. The stimulus generator of claim 10, wherein:

said electrode means includes said case, and further includes a nerve electrode mounted on said selected cranial nerve for application of the electrical stimuli generated by said electronics to the selected cranial nerve.

16. The stimulus generator of claim 10, wherein:

said distinguishing means includes means for identifying a seizure-indicative time rate of change by detecting when a predetermined threshold slope of time rate of change in heart rate is exceeded.

17. A device-implemented method of controlling seizures in an epileptic patient, comprising the steps of:

implanting into the patient a medical device adapted to be selectively activated to generate an electrical waveform constituting a pre-programmed therapy regimen to control epileptic seizures by application of the waveform to modulate electrical activity of the patient's vagus nerve;

detecting time rate of change of cardiac activity of the patient indicative of an imminent epileptic seizure; and responding to the detection of such time rate of change of cardiac activity to automatically activate the device and thereby generate said electrical waveform for application as an electrical stimulus to the vagus nerve.

18. The method of claim 17, including:

detecting a time rate of change of the patient's heart rate relative to a predetermined threshold time rate of change to distinguish seizure-indicative change from physical activity-indicative change.

19. The method of claim 18, wherein:

an imminent seizure is indicated when the time rate of change of the patient's heart rate exceeds said predetermined threshold time rate of change.

20. The method of claim 17, including:

detecting a time rate of change of the patient's heart rate indicative of an imminent seizure by a spectral analysis of cardiac activity.

21. The method of claim 20, wherein:

a time rate of change of the patient's heart rate indicative of an imminent seizure is detected by a spectral analysis of cardiac activity exhibiting an increasing peak in the high frequency portion of the spectrum.

22. The method of claim 17, including:

detecting sustained cardiac activity at the highest heart rate detected in said change as a confirmation of imminent seizure.

23. The method of claim 22, including:

generating a pulse burst as said electrical waveform.

24. The method of claim 23, including:

programming a minimum time interval between consecutive ones of said pulse bursts to avoid overstimulation of the nerve.

25. The method of claim 17, including:

detecting cardiac activity of the patient with electrodes integral with the device having sensitivity substantially independent of orientation of the implanted device in the patient.

26. The method of claim 17, including:

detecting cardiac activity of the patient with electrodes including an electrode for use in applying said waveform as an electrical stimulus to the vagus nerve.

27. The method of claim 26, including:

electrically insulating part of the device housing to preclude muscle stimulation.

\* \* \* \* \*